(12) United States Patent
Jin et al.

(10) Patent No.: US 7,608,220 B2
(45) Date of Patent: Oct. 27, 2009

(54) BLOOD SMEAR PREPARATION DEVICE

(75) Inventors: Ying Jin, Shenzhen (CN); Quan Gan, Shenzhen (CN)

(73) Assignee: Shenzhen Mindray Bio-Medical Electronics, Co., Ltd. (CN)

( * ) Notice: Subject to any disclaimer, the term of this patent is extended or adjusted under 35 U.S.C. 154(b) by 2 days.

(21) Appl. No.: 11/508,088

(22) Filed: Aug. 22, 2006

(65) Prior Publication Data

US 2007/0140903 A1 Jun. 21, 2007

(30) Foreign Application Priority Data

Dec. 21, 2005 (CN) .................... 2005 2 0036668 U (51) Int. Cl.
*G01N 21/00* (2006.01)
(52) U.S. Cl. ........................................................ 422/63
(58) Field of Classification Search .................... 422/63
See application file for complete search history.

(56) References Cited

U.S. PATENT DOCUMENTS

| 5,209,903 | A | * | 5/1993 | Kanamori et al. | ............. 422/65 |
| 5,676,910 | A | * | 10/1997 | Levine et al. | .................. 422/65 |
| 5,854,075 | A | | 12/1998 | Levine et al. | |
| 6,319,470 | B1 | | 11/2001 | Lefevre et al. | |
| 2003/0003022 | A1 | * | 1/2003 | Tamura et al. | ................. 422/99 |

FOREIGN PATENT DOCUMENTS

CN 88207465.2 6/1989
CN 93203464.0 1/1994
WO WO 9828603 A1 * 7/1998

OTHER PUBLICATIONS

SIPO Search Report for corresponding Chinese application, 4 pages, dated Jun. 1, 2006.
English translation of abstract for Chinese Patent Application No. 88207465.2.
English transalation of abstract for Chinese Patent Publication No. 93203464.0.

* cited by examiner

*Primary Examiner*—Walter D Griffin
*Assistant Examiner*—Bobby Ramdhanie
(74) *Attorney, Agent, or Firm*—Vista IP Law Group, LLP.

(57) ABSTRACT

A blood smear preparation device includes a base; a carrying table for carrying a microscope slide thereon and being supported on the base; a lifting mechanism mounted to the base; a retaining stand suspended from an output end of the lifting mechanism; a spreader holder rotatably suspended from the retaining stand about a second rotating shaft and positioned above the carrying table; a positioning member for positioning the spreader; and a torsion elastic member provided about the second rotating shaft, with a free end of the torsion elastic member abutting against the spreader holder. With the provision of the second rotating shaft and the torsion elastic member, the spreader has a certain degree of flexibility and self-adaptiveness. Even if the spreader or the microscope slide has no good micro-flatness or straightness, the device may automatically adjust the positions of the spreader and the microscope slide to achieve a line contact and a surface contact, and thus ensure the quality of the blood smear.

21 Claims, 6 Drawing Sheets

BLOOD SMEAR PREPARATION DEVICE

TECHNICAL FIELD

The present subject matter relates to a blood smear preparation device.

BACKGROUND ART

In the prior art, two types of schemes, namely the centrifugation technology and the wedge technology, are employed to prepare blood smears, which are to be observed with a microscope.

A process employing the centrifugation technology comprises the following steps, placing a microscope slide in a sealed container having a rotatable disc, dropping blood onto the microscope slide, rotating the rotatable disc to drive the microscope slide to rotate together so as to swing off redundant blood, such that a blood film of monolayer cell is formed on the surface of the microscope slide. However, this technology has the following disadvantages: 1) the interior of the container is contaminated each time after a blood smear is prepared, and it is difficult to clean the container automatically, and 2) although a shield may be provided outside the rotatable disc to form the sealed environment, a large amount of floating blood particles (floating masses) are generated within the shield during a high speed rotating period, and the shield is unable to prevent the floating masses from diffusing into the air, and the blood, if it is pathogenic, would put the lab staffs in great danger. Even though the above problems could be solved, it will result in high production cost and thus is impractical.

Figure 1:
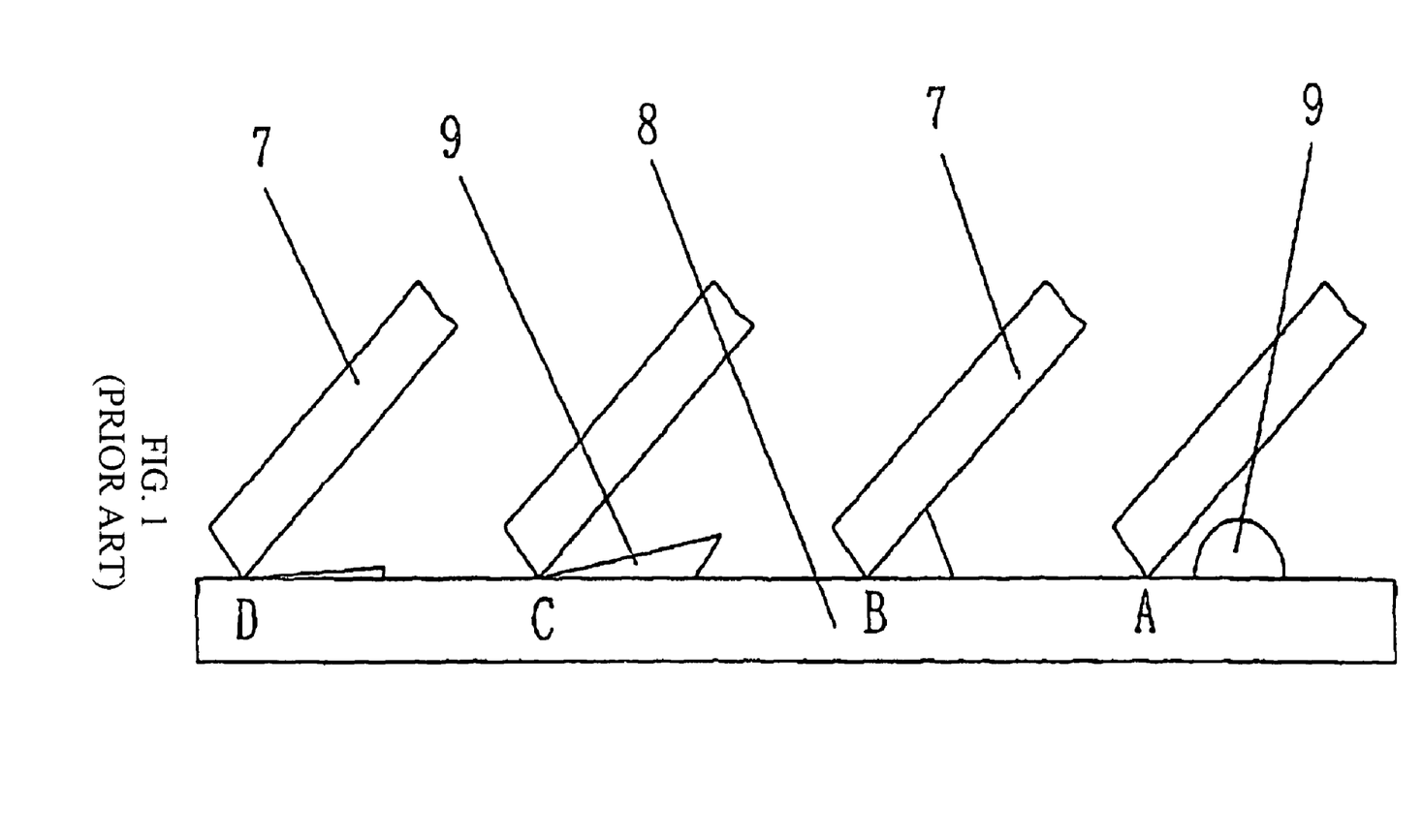
FIG. 1 is a schematic view of a process of preparing a smear employing the prior wedge technology.

Referring to FIG. 1, a process employing the wedge technology comprises the following steps. First, a certain amount of blood 9 is dripped onto a microscope slide 8 at the position A. Secondly, blood 9 is contacted by an edge of a spreader 7, such that blood 9 is diffused along the edge of the spreader 7 (at the position B). At last, the spreader 7 draws blood 9 such that the suction among the blood cells drives the blood to form a uniform blood film on the microscope slide 8 (at positions C and D). Such a process utilizing a spreader has the advantages of being not harmful to the environment and the operator, easy to implement and low in cost.

Comparing the above two schemes with respect to each other, one may find that it is more practical to use the wedge technology to prepare blood smears. Prior art blood smear preparation device employing the wedge technology comprises a spreader retaining plate, a spring mounting rack, a stand for supporting a front end of a spreader and a moving rod for moving the front end of the spreader. The spreader retaining plate is used for retaining the spreader. The spring mounting rack is used for mounting a tension spring, which generates a tension force when the whole spreader retaining means descends to make the spreader contact the microscope slide, such that the spreader presses against the microscope slide with a predetermined pressure. The spreader retaining plate is able to pivot about a pivot point. Two tension springs are fixed to the spreader retaining plate symmetrically. When the whole spreader retaining means descends to make the spreader contact the microscope slide, the spreader pivots about the pivot point in a clockwise direction to pull the two springs downward such that its reaction force makes the spreader to press against the microscope slide with a pressure. Meanwhile, another spring is used to limit the front end of the spreader so as to prevent the spreader retaining plate from pivoting downward about the pivot point without limit when the spreader is in a suspending state. The stand for supporting the front end of the spreader is used to fix the spreader retaining plate and the spring mounting rack. The moving rod for moving the front end of the spreader may drive the spreader retaining plate, the spring mounting rack and the stand for supporting the front end of the spreader to move upward and downward as well as forward and backward. The moving rod may be connected to the stand through a connecting shaft, such that they may rotate about the connecting shaft clockwise and counterclockwise.

However, such a preparation device has the following disadvantages.

1) The structure of the spreader retaining means of the device is complicated and has a high possibility of failure. Since the pressure is adjusted by means of two tension springs, it is difficult to adjust initial tension forces at the time of mounting the springs. Further, another spring is used to limit the front end of the spreader, such that the spreader retaining plate is prevented from pivoting downward about the pivot point without limit when the spreader is is in a suspending state. Since there are too many springs to be used, the possibility of spring failure is increased. In an automatic spreading and dyeing device, the spreader retaining means has the higher possibility of failure when preparing a smear with a spreader, and such a failure is mainly due to spring failure.

2) With respect to the structure of the spreader retaining means, because the spreader presses against the spreader retaining plate tightly and directly, it is impossible to adjust relative positions between the spreader and the microscope slide, and thereby it is impossible to ensure that the edge of the spreader is perpendicular to a long edge of the microscope slide. Manufacture and assembly errors of the front end of the spreader may result in that a short edge of the spreader is not perpendicular to the long edge of the microscope slide, which in turn causes such problems that the blood film is not at the center of the microscope slide, that there is a delay in the movement of the spreader and so on. These problems will affect the quality of the smear adversely.

3) The blood smear preparation device has no good damping capability. As a result, the blood smear has grainy streaks in a longitudinal direction, which will affect the clinical observation unfavorably.

SUMMARY

An object of the present subject matter is to provide an improved blood smear preparation device that can produce a blood smear with a better quality. In one aspect, an object of the present subject matter is to provide a blood smear preparation device that can automatically adjust relative positions between the spreader and the microscope slide so as to ensure a good contact between them. In another aspect, another object of the present subject matter is to improve the structure of a spreader retaining means so that the spreader retaining means has a simple structure and a low possibility of failure, and to ensure that the spreader has certain flexibility and self-adaptiveness and thus the prepared blood smear has a better quality.

According to one embodiment, the blood smear preparation device, comprising a base; a carrying table carrying a microscope slide thereon and being supported on the base; an actuator mounted to the base; and a retaining means for retaining a spreader, the retaining means being pivotably connected to the actuator about a first pivot axis, the retaining means being driven by the actuator so that the spreader contacts the microscope slide with an edge of the spreader and moves relative to the microscope slide; wherein the edge of the spreader is perpendicular to the first pivot axis so that a self-adaptive contact between the spreader and the microscope slide can be achieved when the spreader is contacting and moving relative to the microscope slide.

According to another embodiment, the blood smear preparation device, comprising: a base; a carrying table carrying a microscope slide thereon and being supported on the base; an actuator mounted to the base; a retaining stand; and a holder for mounting a spreader; wherein the actuator is connected with the retaining stand and the holder in sequence, and driving the retaining stand and the holder so that the spreader contacts the microscope slide with an edge of the spreader and moves relative to the microscope slide; the retaining stand is pivotably connected to the holder about a second pivot axis, the second pivot axis being parallel to the edge of the spreader; and the blood smear preparation device further comprises an elastic member with a certain initial stress, the elastic member being provided between the retaining stand and the holder and acting on the holder so that the spreader can press against the microscope slide with a certain pressure.

According to another embodiment, the blood smear preparation device comprises a base; a carrying table for carrying a microscope slide thereon and being supported on the base; a lifting mechanism mounted to the base; a retaining stand suspended from an output end of the lifting mechanism; a spreader holder rotatably suspended from the retaining stand about a second rotating shaft and positioned above the carrying table; a positioning member for positioning the spreader; and a torsion elastic member provided about the second rotating shaft, with a free end of the torsion elastic member abutting against the spreader holder.

Compared with the prior art, the present subject matter has the following advantages. Since the spreader holder is connected with the retaining stand through the second rotating shaft, the spreader may rotate with the spreader holder. At the same time, a torsion elastic member imparts certain flexibility and self-adaptiveness to the spreader, and thus the quality of the smear can be ensured. The retaining stand is rotatable around the first rotating shaft in either a clockwise or a counterclockwise direction, and thus a good contact between the spreader and the microscope slide can be ensured.

DETAILED DESCRIPTION

The blood smear preparation device according to the present subject matter is used to automatically prepare a blood smear from a blood sample by means of a spreader.

Next, referring to FIGS. 2-8, an illustrative structure and an operating process of the blood smear preparation device will be described.

Figure 2:
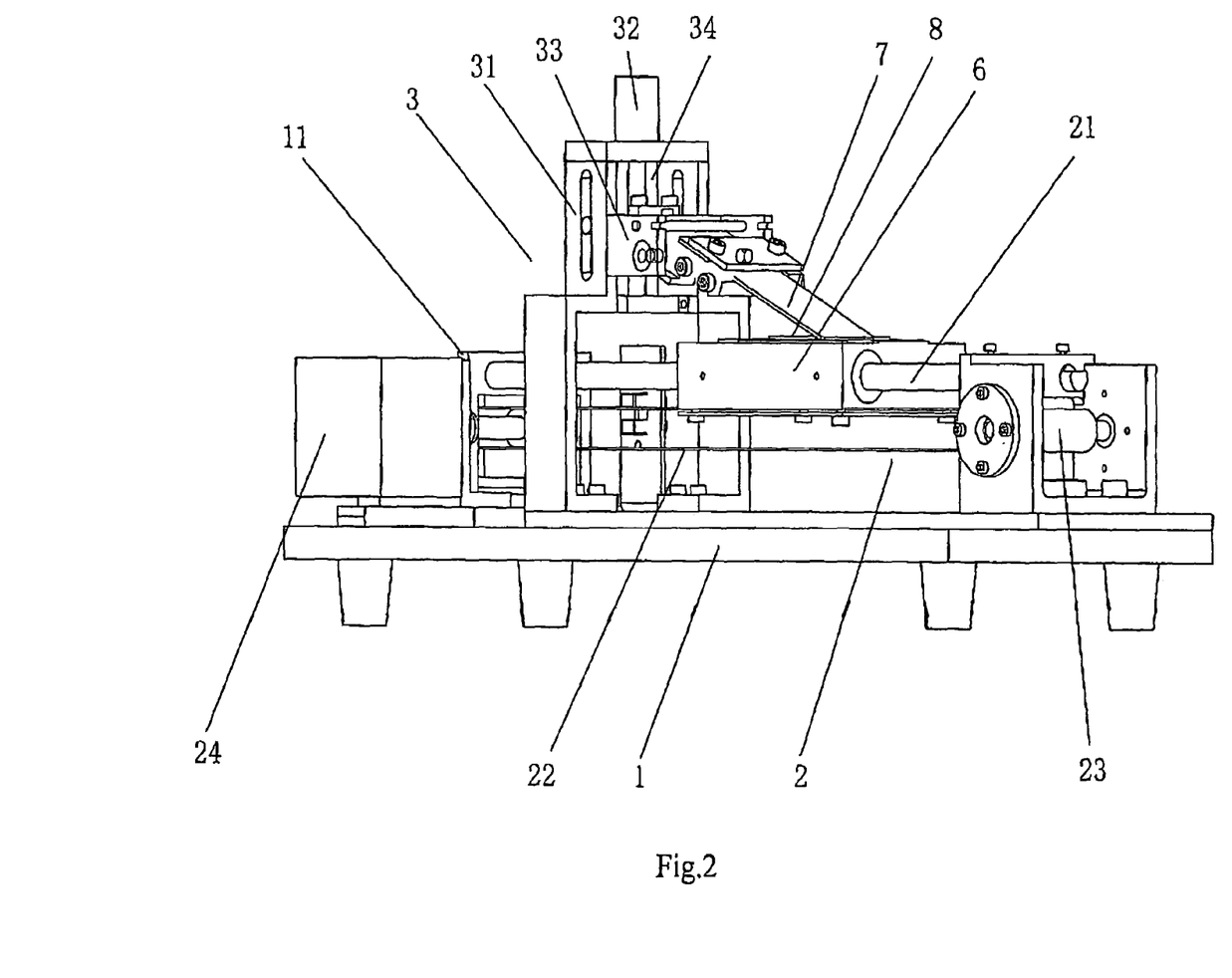
FIG. 2 is a perspective view of the blood smear preparation device according to the present subject matter.
Figure 3:
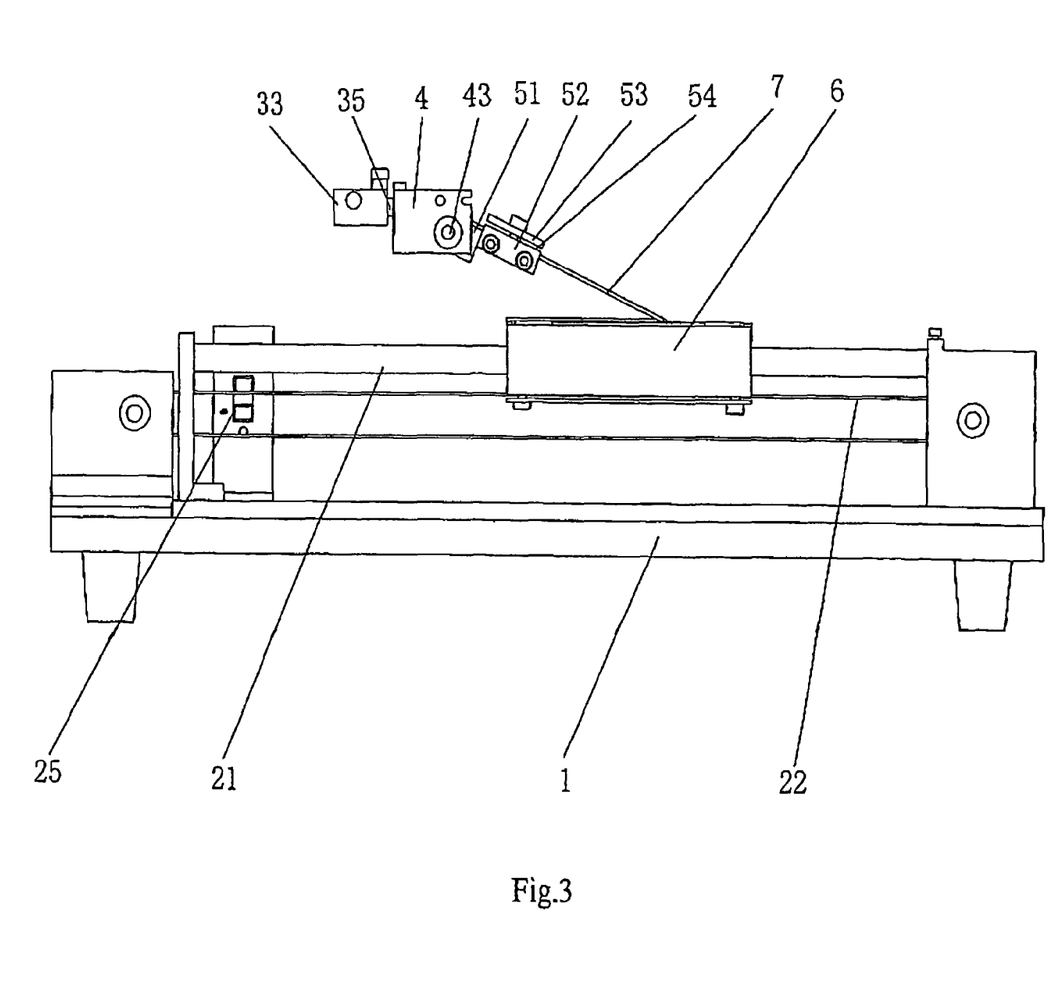
FIG. 3 is a front view of the blood smear preparation device according to the present subject matter.
Figure 4:
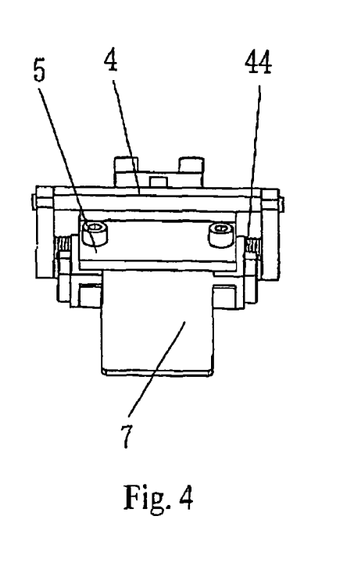
FIGS. 4 to 6 are respectively a right view, a front view and a top view of the assembly of the lifting block, the retaining stand, the spreader holder and a spreader, according to the present subject matter.
Figure 5:
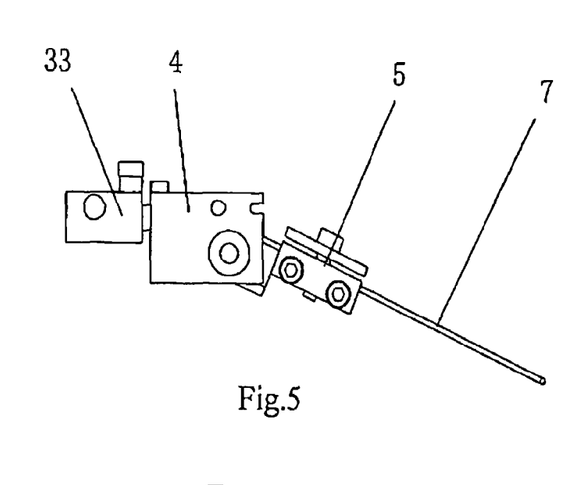
Figure 6:
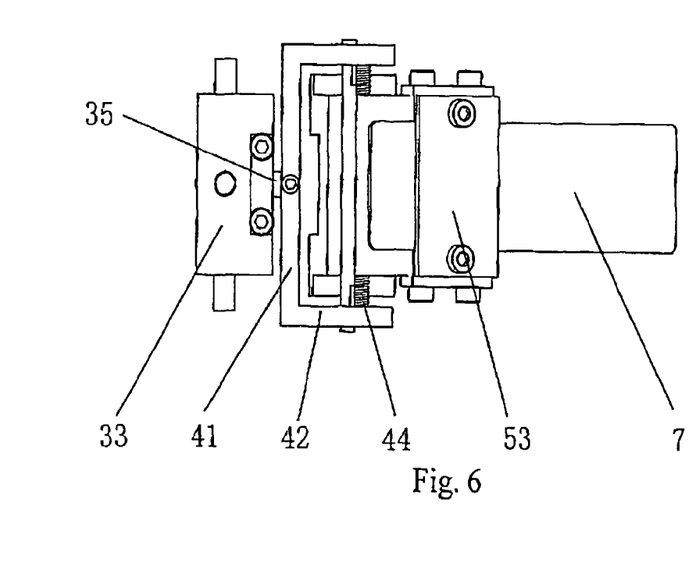
Figure 7:
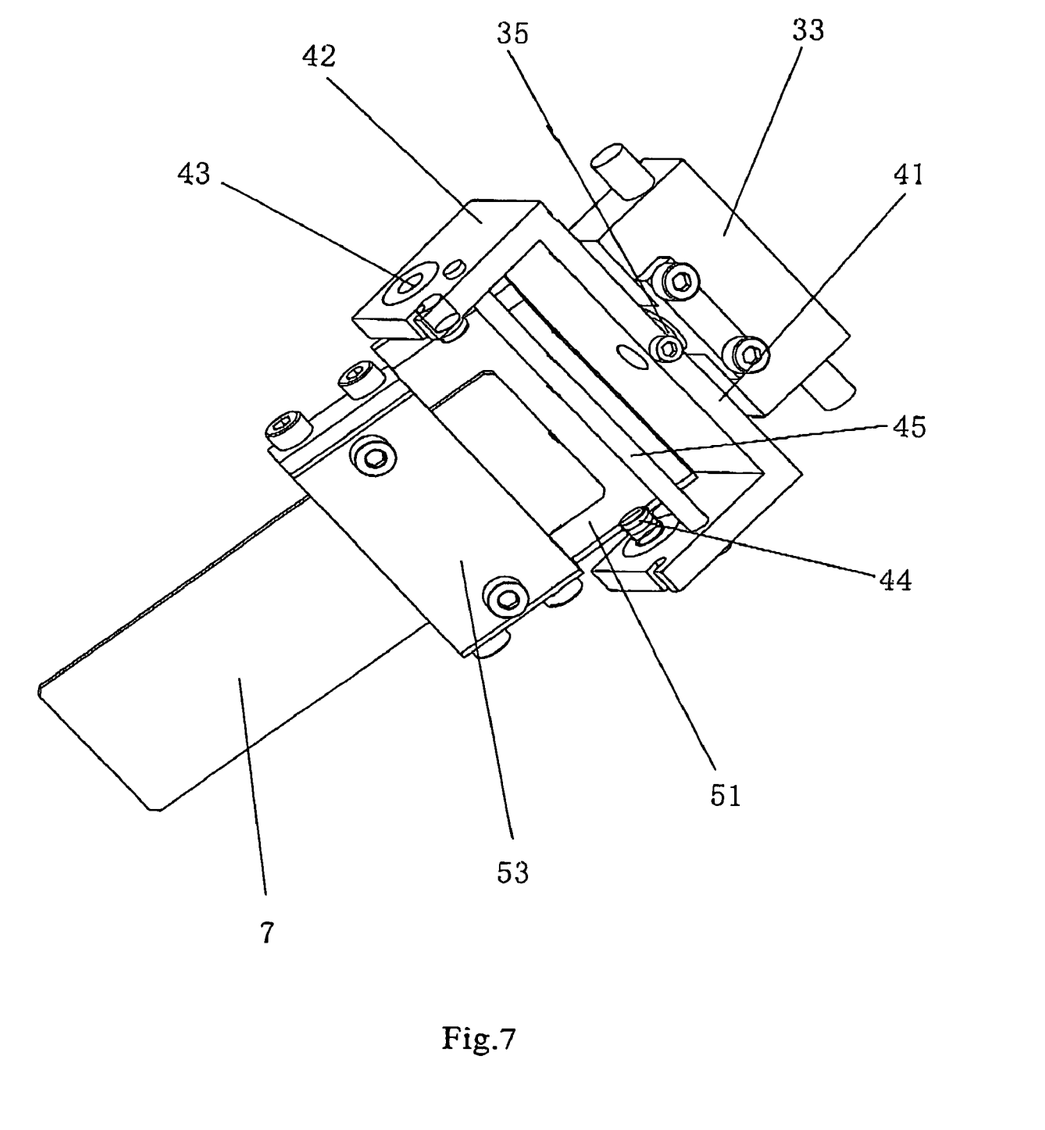
FIG. 7 is a perspective view of the assembly of the lifting block, the retaining stand, the spreader holder and a spreader, according to the present subject matter.

The blood smear preparation device includes a base 1, a carrying table 6 carrying a microscope slide 8, a horizontal transmission mechanism 2, an actuator, and a retaining means. The retaining means comprises a retaining stand 4 and a spreader holder 5. The carrying table 6 is supported on the base 1, and may be driven by the horizontal transmission mechanism 2 to move in a horizontal direction. In one embodiment, the actuator is a lifting mechanism 3 which is mounted to the base 1. The retaining stand 4 is suspended from an output end of the lifting mechanism 3. The spreader holder 5 is positioned above the carrying table 6, suspended from the retaining stand 4 via a pair of rotatable members, and is provided with a positioning member for positioning the spreader. The base 1 is used to support the whole device. The carrying table 6 is used to carry a slide or a microscope slide 8 thereon. The horizontal transmission mechanism 2 serves to drive the microscope slide to reciprocate in a horizontal direction. The lifting mechanism 3 serves to drive the spreader 7 to reciprocate in a vertical direction. The retaining stand 4 is used to connect the spreader holder 5 and the lifting mechanism 3. The spreader holder 5 grips and positions the spreader 7 with a positioning member.

The horizontal transmission mechanism 2 comprises guide levers 21, a timing belt 22, a timing belt pulley 23 and a first motor 24. There are two parallel guide levers 21 being horizontally supported on the bracket 11 of the base 1. The timing belt 22 is located below the guide levers 21 and is tensioned around the timing belt pulley 23. The first motor 24 is installed on the base 1 and may drive the timing belt pulley 23. The carrying table 6 is used to position the microscope slide 8. The center portion of the carrying table 6 movably clamps over the two guide levers 21, and the bottom of the carrying table 6 is fixed on the timing belt 22, such that the carrying table 6 may be driven by the first motor 24 and then may slide along the guide levers 21 in the horizontal direction.

The lifting mechanism 3 comprises a retaining rack 31, a second motor 32, a lifting block 33 for lifting the spreader and a vertical guide rail 34. The retaining rack 31 is vertically mounted to the base 1 and extends across the two guide levers 21. The second motor 32 is installed on the upper portion of the retaining rack 31, and has an output shaft extending downward vertically. The lifting block 33 is fixed at the end of the output shaft of the second motor 32. In order to guide the movement of the lifting block 33, the lifting block 33 may movably fit onto the vertical guide rail 34, such that the lifting block 33 may be driven by the second motor 32 and reciprocate along the guide rail 34 in a vertical direction. In this embodiment, the guide rail 34 is in the form of a lead screw 34.

The retaining stand 4 comprises a base plate 41 and two side plates 42 extending from two opposite sides of the base plate 41. The base plate 41 is connected with the lifting block 33, and the two side plates 42 are connected with the spreader holder 5. The base plate 41 is connected with the lifting block 33 through a first rotating shaft 35. The first rotating shaft 35 has a first pivot axis, is rotatably connected with the lifting block 33 at one end, and is fixedly connected with the base plate 41 at the other end. In this embodiment, the lifting block 33 is provided with a roller bearing therein. An inner race of the roller bearing is set around the one end of the first rotating shaft 35, such that the retaining stand 4 is rotatable around the first rotating shaft 35 in either a clockwise or a counterclockwise direction. It is thereby ensured that, when the spreader 7 contacts the microscope slide 8, the position where the edge of the spreader 7 contacts the microscope slide 8 may be adjusted automatically so as to realize a good contact therebetween.

The spreader holder 5 comprises a supporting plate 51 for supporting the spreader and a positioning member for positioning the spreader. The supporting plate 51 is roatably connected with the two side plates 42 of the retaining stand 4 through two second rotating shafts 43. Each of the second rotating shafts 43 has a second pivot axis. A roller bearing is respectively provided within each of the side plates 42. One end of each of the two second rotating shafts 43 fits tightly against an inner race of the corresponding roller bearing, and the other end thereof is respectively secured to the corresponding side of the supporting plate 51. A middle part of each second rotating shaft 43 is provided with an elastic member. In one embodiment, the elastic member is an elastic torsion member 44. The elastic member may be a torsion spring for example. A free end of each torsion elastic member 44 abuts against the supporting plate 51, and another free end thereof abuts against a fixed member (such as the retaining stand 4). The positioning member comprises a base plate 52 and a cover plate 53. The base plate 52 is fixed to a front end of the supporting plate 51, and the cover plate 53 covers the base plate 52 such that a gap 54, into which the spreader 7 is inserted, is formed between the cover plate 53 and the base plate 52. The gap 54 has a width matching the width of the spreader 7 so as to position the spreader 7 in a width direction, thus ensuring that an edge of the spreader 7 is perpendicular to a long edge of the microscope slide 8.

The spreader 7 is mounted within the spreader holder 5, with a tail portion of the spreader 7 placed on the supporting plate 51, a middle portion of the spreader 7 inserted in the gap 54 and being fastened by the cover plate 53, and a head portion of the spreader 7 suspended and inclined downward toward the microscope slide 8. Thus, the spreader 7 may rotate about the second shafts 43 together with the spreader holder 5 in either a clockwise or counterclockwise direction. In the present embodiment, the gap 54 between the cover plate 53 and the base plate 52 can be adjusted by adjusting the height of the cover plate 53 relative to the base plate 52, so as to be adaptable to various spreaders of different cross-section sizes. In an initial position, the gap may be adjusted to be larger so as to assist the insertion of the spreader 7. After the spreader 7 is inserted, the cover plate 53 may be adjusted to an appropriate position so as to grip the spreader 7 in the gap 54.

The spreader 7 and the microscope slide 8 are both in the form of a glass sheet with eight chamfered edges, such as a common slide with eight chamfered edges, which has a length of 76.2 mm, a width of 25.4 mm and a thickness of 1-1.2 mm. The short edge (25.4 mm) of the spreader 7, as an edge contacting the blood, performs a spreading process during the preparation process of a smear. The edges of the microscope slide or the spreader need to be polished so that they have a good straightness and a good surface roughness.

During the operation of the preparation device, the vibration of the spreader 7 will affect the quality of the smear greatly. Since the torsion elastic member 44 imparts elasticity to the spreader 7, the effect of vibration may be diminished. Therefore, the spreader 7 is floatable, self-adaptive and flexible in the spreading process. Further, after the spreader 7 is lifted from the microscope slide 8, its head portion will rotate downward about the second shafts 43 in the clockwise direction due to its weight. If the torsion elastic member 44 has no initial elastic force, the spreader 7 will rotate too much and cause the torsion elastic member to fail. Therefore, a limit member is provided between the two side plates 42 of the retaining stand 4. The limit member may be a gag lever post or a stop piece. In one embodiment, the limit member is a gag lever post 45. The gag lever post 45 is positioned at a limit position of the supporting plate 51, and can be placed over the tail end of the supporting plate 51 or at a middle position below the supporting plate 51. At the limit position, the torsion elastic member 44 has an initial torsion angle of 10 degree. Due to the gag lever post 45, the torsion elastic member 44 may function in an optimized operation range and has a certain initial elastic force, thus generating a force acting on the spreader 7 during the spreading process. It is ensured that the spreader 7 will not interfere with the carrying table 6 and the guide lever 21, and the head portion may only move upward for a very short distance, thus resulting in a shorter travel of the whole lifting mechanism and a more compact structure. Further, the first pivot axis of the first rotating shaft 35 is non-uniplanarly perpendicular to the second pivot axis of the second rotating shafts 43. Thus, with the provision of the first rotating shaft 35, the spreader 7 may rotate about the first pivot axis parallel with the moving direction of the carrying table 6. With the provision of the second shafts 43, the spreader 7 may rotate about the second pivot axis perpendicular to the first pivot axis. Thus, the spreader may adjust its position in a self-adaptive manner.

Further, the preparation device is provided with a first sensor 25 for controlling an initial position of the carrying table 6, and a second sensor for controlling an initial position of the lifting block 33.

Figure 8:
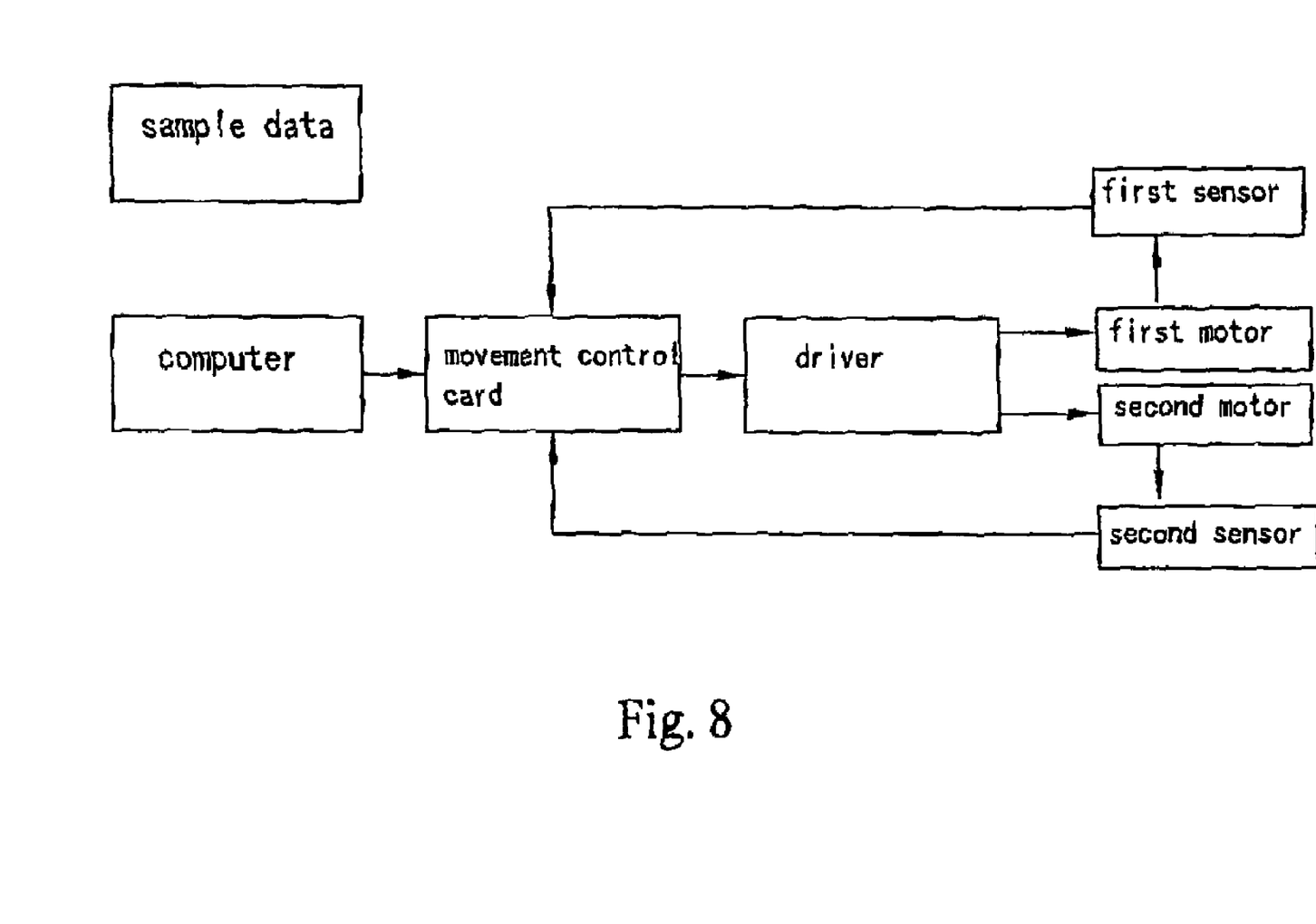
FIG. 8 is a block diagram showing the control principle according to the present subject matter.

Referring to FIG. 8, the control flow chart of the blood smear preparation device is as follows. When the blood smear is to be prepared, sample parameters being obtained by a blood cell analyzer are input into a computer. The computer sends commands, which are going to be performed on basis of the sample, to a fundamental movement control card via a serial port. The control card controls a driver to send impulse signals and makes the first and second motors 24 and 32 to cooperatively operate, so as to finish the spreading process.

The operating time sequence of the blood smear preparation device can be as follows:

1. After the device is started up, search an initial position of the carrying table 6 relative to the spreader 7. If the carrying table 6 is not at the position of the first sensor 25, it will automatically move to the position of the first sensor 25. A hood secured to a side of the carrying table 6 will initiate the first sensor 25 so that the sensor will transmit a signal to the control card, and the control card commands the first motor 24 to stop. After the above steps are finished, liquid such as blood will be dropped onto the microscope slide.

2. Sample parameters (HCT (HEMATOCRIT)) are inputted, and the computer sends serial port protocol to a movement control card. According to command protocol, the control card controls the driver to send impulses and then controls the second motor 32. The second motor 32 moves relevant members to the position of the spreader.

3. The lifting block 33 moves downward until the spreader 7 contacts the microscope slide 8.

4. The carrying table 6 moves until an edge of the spreader 7 contacts the blood. The blood diffuses along the edge of the spreader.

5. The carrying table 6 moves backward so as to form a smear.

6. The second motor 32 drives the lifting block 33 to move upward and thereby lifts the spreader.

7. The carrying table 6 moves to the position of the first sensor 25, and the first sensor 25 is initiated by a hood at a side of the carrying table 6 and sends a signal to the control card. The control card then commands the motor 24 to stop.

In the present subject matter, the blood smear can be prepared through a horizontal reciprocation of the carrying table. Alternatively, the blood smear may be prepared by mounting the lifting mechanism on the guide levers 21 and utilizing the first motor 24 to drive the mechanism and thereby to reciprocate the spreader horizontally. When the spreader reciprocates horizontally, an automatic cleaning device for the spreader may be provided directly in front of a spreader. After the preparation is completed, the first motor may continue to drive the spreader to move forward until moving into the cleaning device. The spreader can be automatically washed and air-dried in the cleaning device. Further, an automatic slide transport line may be added near the carrying table, and it automatically transports the slide onto the carrying table. Thus, an automatic slide loading function can be achieved, and a fully automatic blood smear preparation device is constructed.

In summary, the subject matter provides a blood smear preparation device, which comprises a base 1; a carrying table 6 carrying a microscope slide 8 thereon and being supported on the base 1; an actuator 3 mounted to the base 1; and a retaining means for retaining a spreader 7, the retaining means being pivotably connected to the actuator 3 about a first pivot axis, the retaining means being driven by the actuator 3 so that the spreader 7 contacts the microscope slide 8 with an edge of the spreader 7 and moves relative to the microscope slide 8; wherein the edge of the spreader 7 is perpendicular to the first pivot axis so that a self-adaptive contact between the spreader 7 and the microscope slide 8 can be achieved when the spreader 7 is contacting and moving relative to the microscope slide 8.

Besides, the subject matter provides another blood smear preparation device, which comprises a base 1; a carrying table 6 carrying a microscope slide 8 thereon and being supported on the base 1; an actuator 3 mounted to the base 1; a retaining stand 4; and a holder 5 for mounting a spreader 7; wherein the actuator 3 is connected with the retaining stand 4 and the holder 5 in sequence, and driving the retaining stand 4 and the holder 5 so that the spreader 7 contacts the microscope slide 8 with an edge of the spreader 7 and moves relative to the microscope slide 8; the retaining stand 4 is pivotably connected to the holder 5 about a second pivot axis, the second pivot axis being parallel to the edge of the spreader 7; and the blood smear preparation device further comprises an elastic member 44 with a certain initial stress, the elastic member 44 being provided between the retaining stand 4 and the holder 5 and acting on the holder 5 so that the spreader 7 can press against the microscope slide 8 with a certain pressure.

What is claimed is:

1. A blood smear preparation device, comprising:
   a base;
   a carrying table carrying a microscope slide thereon and being supported on the base;
   an actuator mounted to the base; and
   a retaining means for retaining a spreader, the retaining means being pivotably connected about a first pivot axis to the actuator, the retaining means being driven by the actuator so that the spreader contacts the microscope slide with an edge of the spreader and moves relative to the microscope slide, wherein
   the blood smear preparation device is configured for rotating or pivoting the spreader about or around the first pivot axis and a second pivot axis to cause the edge to contact the microscope slide for blood smear preparation, wherein the second pivot axis is perpendicular to the first pivot axis.

2. The blood smear preparation device according to claim 1, wherein:
   the retaining means comprises a retaining stand and a holder, the holder being used for directly retaining the spreader and pivotably connected to the retaining stand about a second pivot axis which is parallel to the edge of the spreader; and
   the retaining means further comprises an elastic member with a certain initial stress, the elastic member being provided between the retaining stand and the holder and acting on the holder so that the spreader can press against the microscope slide with a certain pressure.

3. The blood smear preparation device according to claim 2, further comprising a limit member secured to the actuator or the retaining stand so as to limit an initial angular orientation of the holder.

4. The blood smear preparation device according to claim 2, wherein the elastic member comprises a torsion spring, one end of the torsion spring being fixed and the other end of the torsion spring being a free end abutting against the retaining stand or the holder.

5. The blood smear preparation device according to claim 1, wherein the actuator comprises a lifting mechanism for lifting the retaining means upward and downward.

6. A blood smear preparation device, comprising:
   a base;
   a carrying table carrying a microscope slide thereon and being supported on the base;
   an actuator mounted to the base;
   a retaining stand; and
   a holder for mounting a spreader, wherein
   the actuator is connected with the retaining stand and the holder in sequence, and driving the retaining stand and the holder so that the spreader contacts the microscope slide with an edge of the spreader and moves relative to the microscope slide,
   the retaining stand is pivotably connected to the holder about a first pivot axis, and
   the blood smear preparation device further comprises an elastic member with a certain initial stress, the elastic member being provided between the retaining stand and the holder and acting on the holder so that the spreader can press against the microscope slide with a pressure, wherein
   the blood smear preparation device is configured for rotating or pivoting the spreader around or about the first pivot axis and a second pivot axis to cause the edge to contact the microscope slide for blood smear preparation, wherein the second pivot axis is perpendicular to the first pivot axis.

7. The blood smear preparation device according to claim 6, further comprising a limit member secured to the actuator or the retaining stand so as to limit an initial angular orientation of the holder.

8. The blood smear preparation device according to claim 6, wherein the elastic member comprises a torsion spring, one end of the torsion spring being fixed and the other end of the torsion spring being a free end abutting against the retaining stand or the holder.

9. The blood smear preparation device according to claim 6, wherein the actuator is pivotably connected with the retaining stand about a first pivot axis, the first pivot axis being perpendicular to the edge of the spreader so that a self-adaptive contact between the spreader and the microscope slide can be achieved when the spreader is contacting and moving relative to the microscope slide.

10. The blood smear preparation device according to claim 6, wherein the actuator comprises a lifting mechanism for lifting the retaining stand upward and downward.

11. The blood smear preparation device according to claim 10, further comprising a guide rail and a transmission member, both of them mounted to the base, and the transmission member driving the lifting mechanism or the carrying table to move along the guide rail in a horizontal direction.

12. The blood smear preparation device according to claim 6, further comprising a cleaning device for automatically washing and air drying the spreader.

13. A blood smear preparation device, comprising:
a base;
a carrying table for carrying a microscope slide thereon and being supported on the base;
a lifting mechanism mounted to the base;
a retaining stand suspended from an output end of the lifting mechanism;
a spreader holder rotatably suspended from the retaining stand about a second rotating shaft and positioned above the carrying table;
a positioning member for positioning the spreader, wherein the spreader holder is configured for rotating or pivoting the spreader around or about a first pivot axis and a second pivot axis to cause an edge of the spreader to contact the microscope slide for blood smear preparation, wherein the second pivot axis is perpendicular to the first pivot axis; and
a torsion elastic member provided about the second rotating shaft, with a free end of the torsion elastic member abutting against the spreader holder.

14. The blood smear preparation device according to claim 13, wherein the retaining stand is provided with a gag lever post positioned at a terminal location of movement travel of the spreader holder.

15. The blood smear preparation device according to claim 13, wherein the positioning member comprises a base plate and a cover plate, with a gap for inserting the spreader formed between the base plate and the cover plate, and the cross-sections of the gap and the spreader matching each other in size.

16. The blood smear preparation device according to claim 15, wherein the spreader is located in the gap and inclines downward toward the carrying table.

17. The blood smear preparation device according to claim 13, wherein the lifting mechanism comprises a fixed rack, a driving member, and a lifting block for lifting the spreader, the fixed rack being mounted to the base, the driving member being installed on an upper portion of the fixed rack, the lifting block being connected with a vertical output shaft of the driving member, and the retaining stand being connected with the lifting block.

18. The blood smear preparation device according to claim 17, wherein the retaining stand is rotatably mounted to the lifting block about a first rotating shaft.

19. The blood smear preparation device according to claim 18, wherein the first rotating shaft is non-coplanarly perpendicular to the second rotating shaft.

20. The blood smear preparation device according to claim 13, further comprising a horizontal guide rail and a horizontal transmission member, both of them mounted to the base, with one of the lifting mechanism and the carrying table being movably mounted to the horizontal guide rail and being driven by the horizontal transmission member.

21. A blood smear preparation device, comprising:
a base;
a carrying table for carrying a microscope slide thereon and being supported on the base;
a lifting mechanism mounted to the base;
a retaining stand suspended from an output end of the lifting mechanism, wherein the retaining stand is provided with a gag lever post positioned at a terminal location of travel of the spreader holder;
a spreader holder rotatably suspended from the retaining stand about a second rotating shaft and positioned above the carrying table;
a positioning member for positioning the spreader; and
a torsion elastic member provided about the second rotating shaft, with a free end of the torsion elastic member abutting against the spreader holder.

* * * * *

UNITED STATES PATENT AND TRADEMARK OFFICE
CERTIFICATE OF CORRECTION

PATENT NO.       : 7,608,220 B2
APPLICATION NO.  : 11/508088
DATED            : October 27, 2009
INVENTOR(S)      : Jin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 16 days.

Signed and Sealed this

Twelfth Day of October, 2010

David J. Kappos
*Director of the United States Patent and Trademark Office*